(12) United States Patent
Lin et al.

(10) Patent No.: US 7,396,656 B2
(45) Date of Patent: Jul. 8, 2008

(54) METHOD OF CROSS-LINKING PEPTIDES

(75) Inventors: Han-Jia Lin, Taipei (TW); Yee-Hsiung Chen, Taipei (TW)

(73) Assignee: Academia Sinica, Nankang, Taipei (TW)

( * ) Notice: Subject to any disclaimer, the term of this patent is extended or adjusted under 35 U.S.C. 154(b) by 0 days.

(21) Appl. No.: 11/649,176

(22) Filed: Jan. 3, 2007

(65) Prior Publication Data

US 2007/0190616 A1 Aug. 16, 2007

Related U.S. Application Data

(62) Division of application No. 10/307,562, filed on Nov. 25, 2002, now abandoned.

(51) Int. Cl.
*C12Q 1/48* (2006.01)
*C12N 9/00* (2006.01)
*C12N 9/10* (2006.01)
*C07K 1/00* (2006.01)

(52) U.S. Cl. .................. 435/15; 530/350; 435/183; 435/193

(58) Field of Classification Search .......... 530/350; 435/183, 193, 15
See application file for complete search history.

(56) References Cited

U.S. PATENT DOCUMENTS 5,428,014 A 6/1995 Labroo et al.
5,939,385 A 8/1999 Labroo et al.

OTHER PUBLICATIONS

S. E. Harris, et al., "Structural Characterization of the Rat Seminal Vesicle Secretion II Protein and Gene", The Journal of Biological Chemistry, vol. 265, No. 17, pp. 9896-9903, 1990.
A. Lundwall et al., "Chemical Characterization of the Predominant Proteins Secreted by Mouse Seminal Vesicles", Eur. J. Biochem, 249, pp. 39-44, (1997).

*Primary Examiner*—Maryam Monshipouri
(74) *Attorney, Agent, or Firm*—Cohen Pontani Lieberman & Pavane LLP

(57) ABSTRACT

A method of cross-linking a peptide to form a homopolymer of the peptide, to immobilize the peptide on a solid phase and to enhance antigenicity of the peptide is disclosed. The method comprises the steps of preparing a fusion peptide by incorporating a cross-linking segment including a tetrapeptide sequence Q-X-K-(S/T) (SEQ ID NO: 15) into the peptide and cross-linking the peptide by a glutaminase.

8 Claims, 4 Drawing Sheets

Fig.1

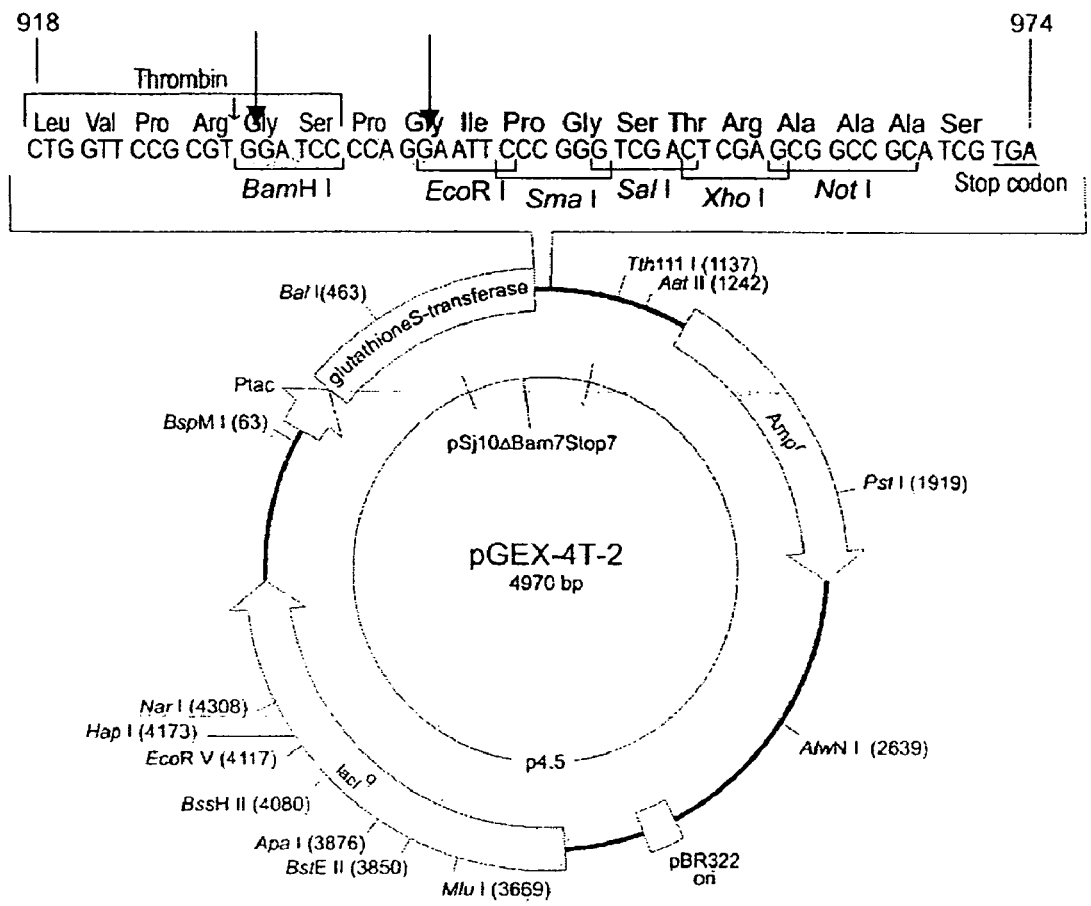

FP#1

5'- gatcccaaataaaatccg    - 3'
3'-     ggtttattttaggcttaa -5'

Q—I—K--S

FP#2

5'-gatcccaaataaaatcccaaactcaagtaaaatcctacgcagcccaactgaagtcccaaccaggccagctaaaaaccatagggcaggtgaagtca 3'

3'-    ggtttattttagggtttgagttcattttaggatgcgtcgggttgacttcagggttggtccggtcgatttttggtatcccgtccacttcagtcttaa -5

Q--I--K--S—Q—T--Q—V--K—S—Y—A—A--Q—L--K—S—Q—P—G—Q—L—K—T—I—G—Q—V—K--S

FP#3

5'- gatcccaaataggttccggcactgggggtaggttcctacgcagccggcctgggttccgggccaggcggtctaggtaccatagggggcgtgaagtcag - 3'

3'-    ggtttatccaaggccgtgacccatccaaggatgcgtcggccggacccaaggcccggtccgcagatccatggtatcccccgcacttcagtcttaa -5'

Q--I--G--S—G—T—G—V--G—S—Y—A—A--G—L—G—S—G—P—G—G—L—G—T—I—G—G—V—K--S

US 7,396,656 B2

METHOD OF CROSS-LINKING PEPTIDES

CROSS REFERENCE TO RELATED APPLICATIONS

This application is a Divisional of U.S. patent application Ser. No. 10/307,562, filed in United States on Nov. 25, 2002 now abandoned.

BACKGROUND OF THE INVENTION

1. Field of the Invention

The present invention relates to a method of cross-linking peptides through a novel amino acid sequence Q-X-K-(S/T) (SEQ ID NO: 15), which was initially identified from mouse seminal vesicle secretion (SVS) III protein. The peptides containing Q-X-K-(S/T) (SEQ ID NO: 15) sequence may be cross-linked by any transgluatminase (TGase).

2. Description of the Related Art

Cross-linking of biomolecules has been noted for decades throughout the world of biotechnology. Cross-linking of proteins with different functions can produce a new molecule with multi functions. Enzymes cross-link to a solid phase makes its activity retaining that can reduce manufactory costs. Biomolecules can be cross-linked by chemical reactions while these reactions are not very specific and probably reduced the activity of enzymes. An alternative way to cross-link biomolecules is enzyme-catalyzed reaction.

Transgluatminase (TGase) is a kind of enzyme with the ability to catalyze protein-protein cross-linking reaction. Transglutaminase (TGase) was first reported by Heinrich Waelsch in 1959. He isolated the enzyme from the liver of guinea pig. In the presence of calcium ion, this enzyme shows trans-amidation activity which binding glutamine in proteins to primary amines covalently. Therefore this enzyme was designed as transglutaminase (EC.2.3.2.13). In recent years, more transglutaminases have been purified from different spices and different tissues. Until now, TGases can be divided into five types: (1) tissue type TGase (TG2), which is commonly expressed in all kinds of tissues, might involve cell-programmed death; (2) epidermal TGase (TG1), found in the wounded epidermal tissues, enable epidermal proteins to cross-link into keratin; (3) hair-follicle TGase, found in hair-follicle cell, can cross-link hair protein; (4) plasma factor XIII, when catalyzed by thrombin, it can cross-link fibrin to stabilize the structure of thrombus; (5) prostate TGase (TG4), found in the coagulating gland of rodent, can catalyze seminal vesicle secreted proteins to copulatory plug. Although these different kinds of TGases have great difference in size and sequences, their catalytic mechanisms are similar. Each of them has a cystine residue in their active site and the enzyme activity is calcium dependent. TGase has great usages in industry. For examples: adding TGase to meat will increase its tenacity and savor in food processing; Enzymes can be fixed by cross-linking of TGase in enzyme engineering; TGase has been used to construct tissues' frame in tissue engineering et cetera.

However, there are limits in industrial applications for TGase. First, most TGase was isolated from animal source and they are also difficult to prepare by recombinant techniques. Second, most TGases have specificities to their substrates that limits the application of TGase. J. E. Folk and his group made a series of studies on tissue type TGase of guinea pig's liver and human's plasma factor XIII (Gorman, J. J. and Folk, J. E. 1980. J. Biol. Chem. 2255, 4419-427; Schhrode, J. and Folk, J. E. 1979. J. Biol. Chem. 254, 653-661). Their works may help to understand the substrate specificity of TGase. TGase has two substrates: one is usually defined as glutamine in a peptides chain and serves as an acyl donor; the other should be a primary amine, which serves as an acyl acceptor. TGases demand more specificity of acyl donor than of acyl acceptor in usual. Therefore, lots of polyamines (spermine and histamine for example) also can be acyl acceptors and covalently bind with proteins as a kind of post-translational modification.

Some works have been done to define the effective sites from substrates of TGases to produce cross-linking peptides fragment. For example, in U.S. Pat. No. 5,428,014 and U.S. Pat. No. 5,939,385, peptide sequences from human plasma fibrinogen have been studied. These peptide fragments are proved to be cross-linkable by human plasma factor XIII and this characteristic has been applied in tissue engineering. This invention generalized an S1-Y-S2 formula from plasma fibrinogen. In this case, S1 represents T-I-G-E-G-Q (SEQ ID NO: 10), Y is 0~7 interval amino acids, and S2 is X-K-X-A-G-D-V (SEQ ID NO: 11) (U.S. Pat. No. 5,428,014, claim 1). Yet, this invention didn't define characteristics and effects of the amino acids in Y position. Moreover, the peptide fragments in this invention were only effective under the action of human plasma factor XIII that limits the usage of other sources of TGases and also restricts the utilities of these peptide fragments. Besides, the length of the defined fragment was too long and the reaction efficiency was low.

In the present invention, we have found a better substrate of TGase from other sources. Seminal vesicles secretions of rodent have been reported as good substrate of TGase (Notides, A. C. and Williams-Ashman, H. G. 1967. Proc. Natl. Acad. Sci. U.S.A. 58, 1991-1995). Notides and Williams-Ashman found a protein (18 kDa) secreted from guinea pig's seminal vesicle. This protein can readily be polymerized by a TGase secreted from coagulating gland. Following study also proved that SVS II protein from mouse and rat seminal vesicle secretions are substrates of TGase (Harris, S. E. et. al. 1990. J. Biol. Chem. 265, 9896-9903; Lundwall, A. et al. 1997. Eur. J. Biochem. 249, 39-44). Though human seminal secretions will not solidify to become copulatory plugs, it has been proved that SgI and SgII proteins from human seminal vesicle are also substrates of TGase (Peter, A. et. Al. 1998. Eur. J. Biochem. 252, 216-221). However, the molecular mechanism of these proteins have never been studied. In this invention, we isolated a new protein, SVS III, from mouse seminal vesicle and proved it a good substrate of transglutaminase. The present invention also provides an effective sequence from SVS III and related applications.

SUMMARY OF THE INVENTION

The purpose of this invention is to take the reactive site in SVS III protein as the substrate of transglutaminase. It provides a novel way to cross-link, fix or polymerize proteins by TGase. The present invention defines the reactive site of TGase from mouse SVS III gene sequence (SEQ ID NO: 1). The minimum effective unit of reaction site includes four amino acids (SEQ ID NO: 15), which are defined as Q-X-K-(S/T). Q represents glutamine, X represents aliphatic side chain of amino acids (Leu, Val, lie, Ala etc., for example); K is lysine; (S/T) can be serine or threonine. The examples of this invention claim that the minimum effective unit can be the substrate of TGase.

When peptides have repetitive minimum effective units (SEQ ID NO: 3 including five minimum effective units, for example), they are better substrates of TGase.

Examples in this invention claim that the rearranged sequence of minimum effective unit (SEQ ID NO: 4) also can be the substrate of TGase. "Cross-linking fragment" is defined as peptides with one or more minimum effective unit or with deformed sequence. Accordingly, the present invention encompasses a peptide for cross-linking, comprising a -QX- sequence at the N-terminal and a -XK(S/T) sequence at the C-terminal, wherein Q is glutamine, X is an amino acid having an aliphatic side chain, K is lysine and (S/T) is either serine or threonine.

Examples in this invention also prove that the cross-linking fragment is a good substrate for TGase from different sources including plasma factor XIII, TGase of guinea pig and TGase in mouse coagulate land secretion.

This peptide fragment can be synthesized directly (Merrifiedid, R. B. 1963. J. Amer. Chem. Soc. 85, 2149-2154), or produced by constructing the cDNA sequence in recombinant plasmid to produce fusion protein. In examples of this invention, we construct the cDNA sequence in recombinant plasmid to produce fusion protein with this cross-linking fragment. Therefore, the fusion protein has the ability to cross-link by TGase. In examples of this invention, we explain how to produce a fusion protein with cross-linking fragment.

The fusion protein containing the cross-linking fragment can be cross-linked to the plastic surface with primary amine by TGase, which retains its enzyme activity.

In examples of this invention, we also proved that fusion protein with the cross-linking fragment could become polymer, which can induce stronger immune reaction when it is injected into animals as an antigen. This method makes an improvement on the production of vaccines.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 1 depicts construction of the recombinant plasmid, where (A) is a map of the recombinant expression vector, pGEX-4T and the sites of restriction enzymes recognized, and (B) shows sequences (SEQ ID NOS 2-9 & 12-14) of each pair of synthesized nucleotides in each clone were aligned in the annealed form;

DETAILED DESCRIPTION OF THE PRESENTLY PREFERRED EMBODIMENTS

Figure 2:
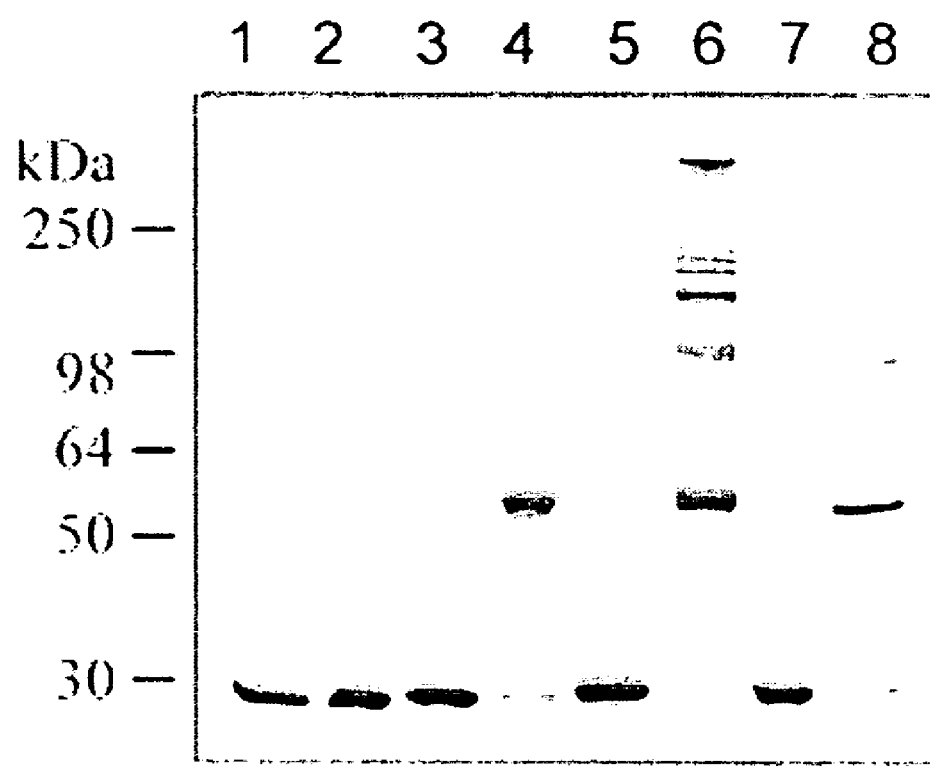
FIG. 2 shows cross-linking of GST fusion proteins by guinea pig liver transglutaminase, where GST protein (lanes 1 and 2), FP#1 (lanes 3 and 4), FP#2 (lanes 5 and 6) and FP#3 (lanes 7 and 8) were cross-linked by guinea pig liver transglutaminase in a reaction buffer (50 mM Tris-HCl, 150 mM NaCl and 7.5 mM CaCl2) with (lanes 1, 3, 5, and 7) or without (lanes 2, 4, 6 and 8) 50 mM EDTA.

As used herein, the terms "cross-linking fragment", "cross-linking sequence", "cross-linking segment", or "minimum effective unit" means the peptide having a Q-X-K-(S/T) (SEQ ID NO: 15) sequence, wherein Q represents glutamine, X represents amino acids having an aliphatic side chain such as Leu, Val, Ile, Ala etc.; K is lysine; (S/T) can be either serine or threonine; the term "fusion protein", "fusion peptide" or "fusion polypeptide" means a peptide containing fragments from different origins.

"TGase" represents transglutaminase;

"GST" represents glutathione S-transferase.

The present invention is further explained and illustrated in the following examples, which represent particular embodiments of, but not limitations to, the present invention.

EXAMPLE 1

Preparation of Fusion Proteins Containing Cross-Linking Effective Sequence

All fusion proteins identified in the present invention were prepared by inserting a cross-linking fragment into GST sequence by recombinant DNA technology. E. Coli expression vector, pGEX4-T (Amersham-Pharmacia, Freiburg, Germany), was used to produce fusion proteins. Restriction enzymes, Bam HI and EcoRI, were used to cut the pGEX4-T vector. To remove the restriction enzymes and small nucleotides, the vector was then purified by 1% agarose gel electrophoresis and recovered from the gel by QiagelElution kit (Qiagen, Hilden, Germany). A sense and an anti-sense DNA fragment encoded each protein fragment were synthesized based on mouse SVS III cDNA (SEQ ID NO: 1). At the beginning and the end of each DNA fragment, a BamHI site and an EcoRI site were added during nucleotide synthesizing (cf. FIG. 1). 20 μl of both strands of the synthesized oligonucleotides, in the concentration of 100 μM, were mixed together and heated to 95° C. for 10 min, then annealed at 55° C. for 10 min and room temperature for another 10 min. The annealed insert DNA fragment was mix with the BamHI/EcoRI-treated pGEX4-T vector and reacted by T4 DNA ligase at 4° C. overnight. The reaction mixture was use to transform host cells, E. Coli strain JM109, by conventional transformation technology. Positive clones, which were able to produce a fusion polypeptide were screened and identified by DNA sequencing.

To produce the recombinant proteins, each bacteria clone was transferred into 100 ml of LB broth containing 100 μg/ml ampicillin and cultured at 37° C. with 200 rpm shaking overnight. The bacteria broth was subcultured in 900 ml LB medium containing 100 μg/ml ampicillin in the next morning. When $OD_{600}$ of the bacteria broth reached 0.6, IPTG (0.5 mM of final conc.) were added into the broth and continuously cultured at 37° C. with 200 rpm shaking for 5 hours. Then the broth was centrifuged at 5,000 rpm for 10 min and discarded the supernatant. The pellet was resuspensed by 10 ml of phosphate buffer saline and mixed with complete protease inhibitor cocktail (Roch, Germany). The bacteria suspension was sonicated for 5 min and the cell lysate was centrifuged at 15,000 rpm for 20 min. The supernatant, so-called the crude extract, was collected for further purification.

The fusion proteins were purified from the crude extract by affinity chromatography on a column of glutathione agarose bead (Amersham-Pharmacia, Freiburg, Germany). Glutathione agarose was packaged into a column with 20 mm inner diagram. The height of the gel was 40 mm. 50 ml of phosphate buffer saline was flowed through the column for equivalence. The crude extract was loaded into the column and then another 50 ml of PBS was flowed through to wash out unbound proteins. Finally, 20 ml of elution buffer (10 mM reduction form glutathione in PBS) was applied into the column and the purified protein was collected. After dialysis and measuring protein concentration, the recombinant proteins were adjusted to 1 µg/ml and stored in −20° C.

EXAMPLE 2

Cross-Linking Ability of the Fusion Proteins

To test the cross-linking abilities of different fusion proteins produced in Example 1, each fusion protein was mixed with tissue transglutaminase from guinea pig's liver in 40 µl reaction buffer (50 mM Tris-HCl, 150 mM NaCl and 7.5 mM $CaCl_2$ pH7.5) and the reaction mixture was incubated at 37° C. for 1 hour. Since the action of transglutaminase is calcium dependent, every experiment had a control, which substitute 50 mM EDTA for 7.5 mM $CaCl_2$. After 1 hour of incubation, 40 µl of 2× Laemmli sample buffer was added to stop the reaction. Each reaction result was resolved by SDS-PAGE.

As shown in FIG. 2, GST itself is not a substrate of TGase (lane 1) and was not cross-linked by the enzyme, while GST fused with insert SEQ ID NO:2 (Fusion Protein No:1, FP#1, lane 3), SEQ ID NO:3 (FP#2, lane 5) and SEQ ID NO:4 (FP#3, lane 7) showed the ability to be cross-linked by transglutaminase. The presence of EDTA in the reaction mixture prevents the fusion proteins to form polymers, because of the lack of calcium ion. Note worthily, the enzyme-catalyzed cross-links of FP#2 were very striking (cf. lane 5 of FIG. 2). There were almost no FP#2 monomer left after the enzyme reaction. Based on the relation between molecular size and protein mobility on SDS/PAGE, dimmers, trimers, tetramers, pentamers and hexamers of FP#2 were clearly identified. Homopolymers larger than hexamers were also detected. Apparently, FP#2 was intermolecularly cross-linked by the enzyme reaction. FP#1 was cross-linked to a dimer by the enzyme reaction (cf. lane 3 of FIG. 2), manifesting the transglutaminase substrate activity of the short peptide QIKS (SEQ ID NO: 2). Likewise, the enzyme was able to cross-link FP#3, which was a mutant of FP#2 with a QI at the N-terminal and a KS at the C-terminal of the cross-linking segment but the inner glutamine (Q) and lysine (K) residues were replaced by glycine residues. Apparently, the four-peptide segment of Q-X-K-(S/T) (SEQ ID NO: 15) is the essential sequence for cross-linking by transglutaminase. While one segment of Q-X-K-(S/T) (SEQ ID NO: 15) is sufficient for the transglutaminase-catalyzed protein cross-linking, the more Q-X-K-(S/T) (SEQ ID NO: 15) repeats the fusion protein contains, the stronger is the cross-linking ability. The sequence of Q-X-K-(S/T) (SEQ ID NO: 15) can also be rearranged and still maintain its cross-linking ability by transglutaminase.

EXAMPLE 3

Cross-Linking Abilities of the Fusion Proteins by Transglutaminases from Different Sources Fusion proteins containing Q-X-K-(S/T) (SEQ ID NO: 15) sequences are not only cross-linked by guinea pig liver transglutaminase but also good substrates to other types of transglutaminases. Thrombin-activated factor XIII (F), guinea pig liver transglutaminase (T), or mouse coagulating gland fluid (M) was incubated with FP#1 (15 µg) in 40 µl reaction buffer (50 mM Tris-HCl, 150 mM NaCl and 7.5 mM $CaCl_2$ pH7.5) and incubated at 37° C. for 1 hour. Since the action of transglutaminase is calcium dependent, every experiment had a control, which 7.5 mM $CaCl_2$ was substituted by 50 mM EDTA. After 1 hour of incubation, 40 µl of 2× Laemmli sample buffer was added to stop the reaction and the reaction mixture was resolved by SDS/PAGE on a 14% gel slab.

Figure 3:
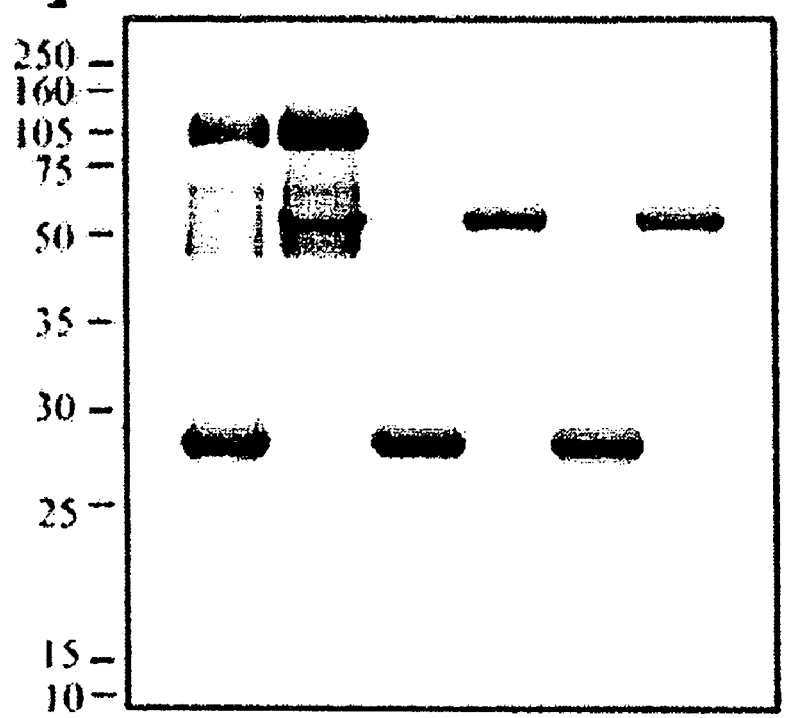
FIG. 3 shows that a fusion protein containing Q-X-K-(S/T) (SEQ ID NO: 15) is a good substrate for different sources of transglutaminase, where FP#1 was cross-linked by different sources of transglutaminases, including mouse coagulating gland fluid (C), human blood factor XIII (F), and guinea pig transglutaminase (T), in a reaction buffer (50 mM Tris-HCl, 150 mM NaCl and 7.5 mM CaCl2) with (lanes 1, 3, and 5) or without (lanes 2, 4, and 6) 50 mM EDTA.

As shown in FIG. 3, FP#1, with the essential sequence of Q-X-K-(S/T) (SEQ ID NO: 15), is a good substrate of transglutaminases from different sources, including mouse coagulating gland transglutaminase (TG4), human blood factor XIII and guinea pig liver transglutaminase (TG2).

EXAMPLE 4

Figure 4:
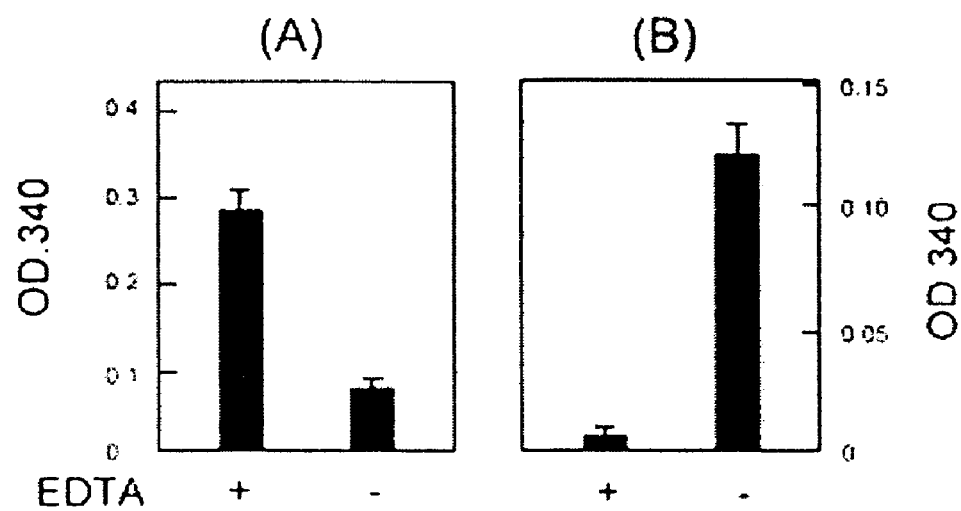
FIG. 4 shows that GST fused with Q-X-K-(S/T) (SEQ ID NO: 15) tandem repeats segment can be fixed on the surface of primary amine containing microplate, where (A) shows GST activity in the reaction mixture after the cross-linking reaction, and (B) shows GST activity in the well of microplate after the cross-linking reaction (see "example 2" for detail experiment condition). This Data represent the means of three experiments, and error bars represent S.D.

Fixation of Fusion Protein Containing Q-X-K-(S/T) (SEQ ID NO: 15) Sequence to a Solid Phase Since transglutaminase has the ability to transfer an acyl group from a molecule to a primary amine so as to form a covalent bond, it is possible to fix a fusion protein which containing Q-X-K-(S/T) (SEQ ID NO: 15) sequence to a solid phase having primary amine on its surface by the action of transglutaminase. In a volume of 50 µl, the reaction mixture contained 1 µg of FP#2. 0.1 µg of guinea pig liver transglutaminase, 50 mM Tris-HCl, 150 mM NaCl and 7.5 mM $CaCl_2$ in pH 7.5. The reaction mixture was loaded into wells of a microplate which contains primary amine on the surface (COSTAR amine surface stripwell, Corning, USA.) and incubated at 37° C. for 2 hrs. As a control, $CaCl_2$ in the reaction was replaced by 50 mM EDTA. After reaction was complete, the supernatant in each well was collected to a microcentrifuge tube and the wells were washed twice by PBS. The supernatant was then mixed with 1 ml of assay reagent (100 mM potassium phosphate buffer pH6.5, 1 mM glutathione, 1 mM 1-Chloro-2,4-dinitrobenzene) to test the enzyme activity of GST. The reaction was carried out 37° C. for 5 min and the absorption at 340 nm was observed. The enzyme activity in the wells were also tested by pouring 100 µl of assay reagent (100 mM potassium phosphate buffer pH6.5, 1 mM glutathione, 1 mM 1-Chloro-2,4-dinitrobenzene) into each well and incubated the plate at 37° C. for 5 min. The solution of each well was collected and its absorption at 340 nm was measured. A stronger absorption represents a higher enzyme activity. The highest enzyme activity was found in the control supernatant (FIG. 4A). However, under the action of transglutaminase, the GST activity of FP#2 was remained in the well of microplate (FIG. 4B). Thus, it demonstrates that transglutaminase can be used to fix a fusion protein having Q-X-K-(S/T) (SEQ ID NO: 15) sequence to a solid phase.

EXAMPLE 5

Polymerization of the Fusion Proteins to Improve Antigenicity

Polymerization of an antigen containing Q-X-K-(S/T) (SEQ ID NO: 15) sequence by transglutaminase can improve antigenicity. In a volume of 50 µl, the reaction mixture contained 50 µg of FP#2 as an antigen, 1 µg of guinea pig liver transglutaminase, 50 mM Tris-HCl, 150 mM NaCl and 7.5 mM $CaCl_2$ pH 7.5. The reaction was carried on at 37° C. for 1 hrs. The $CaCl_2$ in the reaction was replaced by 50 mM EDTA in the control. After the reaction was completed, an equal volume of Freund's incomplete adjuvant was added into each reaction mixture and mixed well with the reaction mixture to form an antigen injection mixture. These antigen injection mixtures were used to inject 12-week-old female mice subcutaneously. Three weeks after the first boost, mice were challenged with the same antigen and received the second challenge after another 3 weeks. The antiserum was collected two weeks after the final challenge. The FP#2 protein was resolved by SDS-PAGE and transferred to a nitrocellulose membrane. After transfer, the protein blots were immunodetected by the Western blotprocedure, using the antiserum as the primary antibody diluted to 1:10000 in a blocking solution (5% nonfat skimmed milk in PBS), and a goat anti-mouse IgG was conjugated with horseradish peroxidase as the secondary antibody diluted to 1:10000 in the blocking solution. The enzyme-staining bands were enhanced by chemiluminescence detection using an ECL kit (Amersham-Pharmacia, Freiburg, Germany) according to the manufacturer's instruction. The result showed a strong immunoreaction to the antigen (FP#2), while the signal in the control serum was weak. Apparently, the antigenicity of the antigen was improved by the polymerization of the FP#2 through the action of transglutaminase.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method of cross-linking a peptide to form polymers of said peptide, comprising the steps of
   (a) incorporating a cross-linking segment comprising the Q-X-K-(S/T) sequence into said peptide to form a fusion polypeptide, wherein Q is glutamine, X is an amino acid having an aliphatic side chain, K is lysine and (S/T) is either serine or threonine; and
   (b) cross-linking said fusion polypeptide with a transglutaminase in a cross-linking reaction buffer to form said polymers.

2. The method of claim 1, wherein said cross-linking segment comprises at least two tandem repeats of said Q-X-K-(S/T) sequence.

3. A fusion polypeptide cross-linked with transglutaminase, wherein the fusion polypeptide comprises a first peptide fragment and a Q-X-K-(S/T) fragment of a different origin from said first peptide fragment, wherein Q is glutamine, X is an amino acid having an aliphatic side chain, and (S/T) is either serine or threonine, said Q-X-K-(S/T) (SEQ ID NO: 15) fragment being incorporated into said first peptide fragment to form said fusion polypeptide.

4. The fusion polypeptide cross-linked with transglutaminase of claim 3, comprising at least two tandem repeats of said Q-X-K-(S/T) fragment.

5. The fusion polypeptide cross-linked with transglutaminase of claim 3, wherein comprising SEQ ID No: 2.

6. A substrate for a transglutaminase, comprising a first peptide fragment and a Q-X-K-(S/T) fragment of a different origin from said first peptide fragment, wherein Q is glutamine, X is an amino acid having an aliphatic side chain, K is lysine and (S/T) is either serine or threonine, said Q-X-K-(S/T) fragment being incorporated into said first peptide fragment to form said substrate for a transglutaminase.

7. The substrate for a transglutaminase of claim 6, comprising SEQ ID No: 2.

8. The substrate for the transglutaminase of claim 6, comprising at least two tandem repeats of said Q-X-K-(S/T) fragment.

* * * * *

SEQUENCE LISTING

```
<160> NUMBER OF SEQ ID NOS: 15

<210> SEQ ID NO 1
<211> LENGTH: 265
<212> TYPE: PRT
<213> ORGANISM: Murine sp.

<400> SEQUENCE: 1

Met Lys Ser Ile Phe Phe Ser Leu Ser Leu Leu Leu Leu Glu Lys
 1               5                  10                  15

Lys Ala Ala Gly Ile Glu Leu Tyr Ala Gly Gly Thr Lys Gly His Phe
            20                  25                  30

Leu Val Lys Thr Ser Pro Leu Met Phe Ile Gly Lys Asn Gln Phe Leu
        35                  40                  45

Tyr Gly His Lys Glu Glu Gln Glu Glu Ala Pro Glu Glu Ser Ile Phe
    50                  55                  60

Val Gln Thr Lys His His Ala Tyr Gly Gln Asp Ala Asp Ala Asp Met
 65                  70                  75                  80

Gly Gly Ala Leu Ser Ser Gln Glu Leu Thr Ser Leu Lys Glu Asp Ile
                85                  90                  95

Val Cys Glu Glu Glu Asp Glu Leu Ala Gln Gln Lys Ser Gln Leu Pro
            100                 105                 110

Ser Gln Ser Gln Ile Lys Ser Gln Thr Gln Val Lys Ser Tyr Ala Ala
        115                 120                 125

Gln Leu Lys Ser Gln Pro Gly Gln Leu Lys Thr Ile Gly Gln Val Lys
    130                 135                 140

Ser Gln Thr Met Leu Lys Ser His Gly Ala Pro Leu Lys Ser Phe Lys
145                 150                 155                 160

Ala Arg Leu Asn Leu Arg Glu Asp Ile Pro Gln Gln Val Lys Gly Arg
                165                 170                 175

Gly Tyr Gly Leu Ala Glu Asp Leu Ala Gln Val Arg Gln Gln Pro Ala
            180                 185                 190

Lys Val His Arg Leu Lys Gly Lys His Arg Gln Ser Arg Lys Thr Ala
        195                 200                 205
```

-continued

```
Ala Phe Tyr Pro Gln Phe Arg Arg His Ser Arg Pro Tyr Pro Arg Tyr
    210                 215                 220

Phe Val Gln Phe Gln Glu Gln Leu Gln Gly Ser Val His His Thr Lys
225                 230                 235                 240

Ser Phe Tyr Pro Gly Pro Gly Met Cys Tyr Cys Pro Arg Gly Gly Val
                245                 250                 255

Ile Leu Tyr Gln Asp Ala Phe Thr Asp
            260                 265

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ile Lys Ser
  1

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Lys Ser Gln Thr Gln Val Lys Ser Tyr Ala Ala Gln Leu Lys
  1               5                  10                  15

Ser Gln Pro Gly Gln Leu Lys Thr Ile Gly Gln Val Lys Ser
             20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ile Gly Ser Gly Thr Gly Val Gly Ser Tyr Ala Ala Gly Leu Gly
  1               5                  10                  15

Ser Gly Pro Gly Gly Leu Gly Thr Ile Gly Gly Val Lys Ser
             20                  25                  30

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
gatcccaaat aaaatccg                                               18

<210> SEQ ID NO 6
<211> LENGTH: 96
<212> TYPE: DNA
<213> ORGANISM: Artificial Sequence
```

```
<220> FEATURE:
<223> OTHER INFORMATION: Description of Artificial Sequence: Synthetic
      nucleotide sequence

<400> SEQUENCE: 6
gatcccaaat aaaatcccaa actcaagtaa aatcctacgc agcccaactg aagtcccaac    60
caggccagct aaaaaccata gggcaggtga agtcag                             96

<210> SEQ ID NO 7
<211> LENGTH: 96
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 7
gatcccaaat aggttccggc actggggtag gttcctacgc agccggcctg ggttccgggc    60
caggcggtct aggtaccata ggggcgtga agtcag                              96

<210> SEQ ID NO 8
<211> LENGTH: 57
<212> TYPE: DNA
<213> ORGANISM: Artificial Sequence
<220> FEATURE:
<221> NAME/KEY: CDS
<222> LOCATION: (1)..(54)
<220> FEATURE:
<223> OTHER INFORMATION: Description of Artificial Sequence: Primer

<400> SEQUENCE: 8 ctg gtt ccg cgt gga tcc cca gga att ccc ggg tcg act cga gcg gcc    48
Leu Val Pro Arg Gly Ser Pro Gly Ile Pro Gly Ser Thr Arg Ala Ala
  1               5                  10                  15 gca tcg tga                                                         57
Ala Ser

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Val Pro Arg Gly Ser Pro Gly Ile Pro Gly Ser Thr Arg Ala Ala
  1               5                  10                  15

Ala Ser

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ile Gly Glu Gly Gln
  1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (3)
<223> OTHER INFORMATION: Variable amino acid

<400> SEQUENCE: 11

Xaa Lys Xaa Ala Gly Asp Val
  1               5

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
aattcggatt ttatttgg                                                     18

<210> SEQ ID NO 13
<211> LENGTH: 96
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 13
aattctgact tcacctgccc tatggttttt agctggcctg gttgggactt cagttgggct       60
gcgtaggatt ttacttgagt ttgggatttt atttgg                                 96

<210> SEQ ID NO 14
<211> LENGTH: 95
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 14
aattctgact tcacgccccc tatggtacct agacgcctgg cccggaaccc aggccggctg       60
cgtaggaacc taccccagtg ccggaaccta tttgg                                  95

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Ser or Thr

```
<400> SEQUENCE: 15

Gln Xaa Lys Xaa
 1
```